United States Patent
Chiang et al.

(10) Patent No.: US 7,108,789 B2
(45) Date of Patent: *Sep. 19, 2006

(54) HIGH PERFORMANCE CONTINUOUS REACTION/SEPARATION PROCESS USING A CONTINUOUS LIQUID-SOLID CONTACTOR

(75) Inventors: Chen-Chou Chiang, Wexford, PA (US); David L. Fair, Imperial, PA (US)

(73) Assignee: Calgon Carbon Corporation, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/412,502

(22) Filed: Apr. 11, 2003

(65) Prior Publication Data
US 2004/0063992 A1    Apr. 1, 2004

Related U.S. Application Data

(63) Continuation-in-part of application No. 10/207,585, filed on Jul. 29, 2002, and a continuation-in-part of application No. 10/213,580, filed on Aug. 6, 2002.

(51) Int. Cl.
*B01D 15/04* (2006.01)
*C02F 1/44* (2006.01)

(52) U.S. Cl. .................. 210/638; 210/749; 210/192; 210/634

(58) Field of Classification Search ............ 210/660, 210/784, 806, 264, 267, 404; 203/10; 261/2; 95/253
See application file for complete search history.

(56) References Cited

U.S. PATENT DOCUMENTS

| | | | |
|---|---|---|---|
| 4,391,997 A | 7/1983 | Mendiratta | |
| 4,400,555 A | 8/1983 | Mendiratta | |
| 4,522,726 A * | 6/1985 | Berry et al. | 210/660 |
| 4,569,371 A | 2/1986 | Dolejs et al. | |
| 4,612,022 A | 9/1986 | Berry | |
| 4,704,262 A | 11/1987 | Berry | |
| 4,764,276 A | 8/1988 | Berry et al. | |
| 4,808,317 A | 2/1989 | Berry et al. | |
| 5,405,992 A | 4/1995 | Funk et al. | |
| 5,502,248 A | 3/1996 | Funk et al. | |

(Continued)

FOREIGN PATENT DOCUMENTS

EP    1 116 508 A1    7/2001

(Continued)

OTHER PUBLICATIONS

Kawase et al., The simulated moving-bed reactor for production of bisphenol A, Catalyst Today, 48(1-4), 199-209.*

(Continued)

*Primary Examiner*—Johann Richter
*Assistant Examiner*—Karl Puttlitz
(74) *Attorney, Agent, or Firm*—Cohen & Grigsby, P.C.

(57) ABSTRACT

A process for reaction and separation which comprises inputting a process material into at least one column of a plurality of columns wherein each column has at least one inlet for accepting flow from another column or group of columns, an external feed stream, an external eluent stream or a combination thereof, and each column has at least one outlet for connecting to another column, a group of columns, an external product stream or a combination thereof. Each column is independently operable in an up-flow or down-flow mode and connected independently to one of the group comprising another column, an external feed stream, an external eluent stream, an external product stream and combinations thereof.

19 Claims, 6 Drawing Sheets

U.S. PATENT DOCUMENTS

| | | |
|---|---|---|
| 5,618,972 A | 4/1997 | Funk et al. |
| 5,676,826 A | 10/1997 | Rossiter et al. |
| 6,114,577 A | 9/2000 | Verhoff et al. |
| 6,431,202 B1 | 8/2002 | Ahlgren et al. |
| 6,576,137 B1 | 6/2003 | Ma |
| 2003/0094416 A1 | 5/2003 | Heikkila et al. |

FOREIGN PATENT DOCUMENTS

| | | | |
|---|---|---|---|
| JP | 11228455 A | * | 8/1999 |
| WO | WO 03/026772 A2 | | 4/2003 |

OTHER PUBLICATIONS

M. Kawase, T.B. Suzuki, K. Inoue, K. Yoshimoto, K. Hashimoto, Chem. Eng. Sci., vol. 51, 2971-2976 (1996).

Kawase, M.; Inoue, Y.; Araki, K.; Hashimoto, K. Catalyst Today 1999, 48, 199-209.

M. Mazzotti, A. Kruglove, B. Neri, D. Gelosa, M. Morbidelli, Chem. Eng. Sci. vol. 51, 1827-1836 (1996).

Ray A., Tonkovich, A.L. Aris, R., Carr, R.W., Chem. Eng. Sci., vol. 45, No. 8 2431-2437 (1990).

A.V. Kruglov, M.C. Bjorklund, R.W. Carr, Chem. Eng. Sci., vol. 51, 2945-2950 (1996).

* cited by examiner

HIGH PERFORMANCE CONTINUOUS REACTION/SEPARATION PROCESS USING A CONTINUOUS LIQUID-SOLID CONTACTOR

CROSS REFERENCE

This application is a continuation-in-part of copending U.S. patent application Ser. No. 10/207,585 filed on Jul. 29, 2002 and a continuation-in-part of copending U.S. patent application Ser. No. 10/213,580 filed on Aug. 6, 2002.

FIELD OF INVENTION

This invention relates to a process for chemical reaction and separation using a liquid-solid contacting system and, more particularly, to a chemical reaction and separation process using a plurality of columns wherein each column can be independently connected and independently operated for flow inlet and outlet, such as with parallel fluid flow, reverse fluid flow or a combination of flow configurations.

BACKGROUND OF THE INVENTION

Combining a process for conducting a continuous reaction with concurrent separation into a single process technique has received renewed attention in recent years. Various reaction/separation technologies are being investigated and have reached differing degrees of development or commercial viability. Fairly developed techniques include, for example, reactive distillation techniques and reactive chromatography. Other techniques, such as reactive membranes and reactive crystallization techniques, are also being developed. Some of these techniques have provided certain benefits such as reduced capital costs, higher productivity, higher product yields and improved selectivity when competing reactions are taking place. For instance, reactive distillation, where simultaneous reaction and distillation separation processes are carried out, has been implemented for the production of methyl acetate. This technique resulted in five times lower investment and five times lower energy use than the traditional two-step process where the reaction is carried out as a first step and the distillation separation is carried out as a separate second step. Despite these advantages, however, the reactive distillation technique has drawbacks, which include temperature sensitivity and azeotrope formation.

Reactive chromatography systems have also been used for conducting combined reaction and separation. Several different reactive chromatography systems have been investigated including a fixed bed with a pressure swing, cylindrical annular bed with a rotating feed input source, a countercurrent moving bed, and a simulated bed. The choice of a particular reaction/separation technology is made based on the specific requirements of specific applications. Each application will have a particular set of requirements in terms of product yield, purity, process productivity, material handling, etc. (See generally, Vaporciyan, G. G., Kadelec, R. H. AIChE J. 1987, 33 (8), 1334–1343; Fish, B. B.; Carr, R. W. Chem. Eng. Sci. 1989, 44, 1773–1783; and Carr, R. W., In Preparative and Production Scale Chromatography, Ganetsos, G., Barker, P. E., Eds.; Chromatographic Science Series Vol. 61; Marcel Dekker Inc.: New York, 1993; Chapter 18.) Traditionally, the preferred method for carrying out continuous reactive chromatography is the simulated moving bed reactor ("SMB") configuration.

Traditional SMB technology (as shown in FIG. 1) comprises a circulation flow path having multiple beds packed with solid separation/catalyst filler connected in series to allow a circulation liquid to be forcibly circulated through the beds in one direction. It also has a port for introducing desorbing liquid into the circulation flow path, an extract port for removing circulation liquid carrying the strongly adsorptive constituents (extracts) from the circulation flow path, a feedstock port for introducing feed stock, which contains the constituents to be separated or reacted and separated, into the circulation flow path, and a raffinate port for removing circulation liquid carrying the weakly adsorptive constituents (raffinate) from the circulation flow path.

As shown in the prior art in FIG. 1, the SMB process is illustrated showing a combined reaction and separation by the general reaction A→B+C. The process is illustrated using four "zones." Typically, although not always, there are two inlets and two outlets in the SMB system unit. The areas defined between them create the four zones. Component A is feed material 11, which is fed into the SMB system between Zone II and Zone III. Component A decomposes to form Component B and Component C. Component B, for example, is the more strongly adsorbed component and therefore moves with the solid in the direction of the extract outlet, which lies between Zone III and Zone IV. At the extract outlet, Component B is collected as extract product 17. Component C is the more weakly adsorbed component and moves with the liquid in the direction of the raffinate outlet, which lies between Zone I and Zone II. At the raffinate outlet, Component C is collected as the raffinate 19 product. The eluent 15 is introduced to the system between Zone I and Zone IV to remove the more strongly adsorbed Component B and to act as the liquid carrier for the system. A number of reactions have been reported:

The SMB process has been demonstrated to increase product yield from equilibrium-limited, liquid phase esterification reactions. Esterification of acetic acid with β-phenethyl alcohol is disclosed in M. Kawase, T. B. Suzuki, K. Inoue, K. Yoshimoto, K. Hashimoto, Chem. Eng. Sci., Vol 51, 2971–2976 (1996). Esterification of acetic acid with ethanol is disclosed in M. Mazzotti, A. Kruglov, B. Neri, D. Gelosa, M. Morbidelli, Chem. Eng. Sci., Vol 51, 1827–1836 (1996); and acetic acid esterification with methanol is disclosed in U.S. Pat. Nos. 5,405,992 and 5,618,972.

U.S. Pat. No. 5,502,248 shows that the equilibrium-limited, liquid phase ester hydrolysis reaction of methyl acetate can be significantly increased through the use of reactive SMB.

Ray A., Tonkovich, A. L., Aris, R., Carr, R. W., Chem. Eng. Sci., Vol. 45, No. 8, 2431–2437 (1990) demonstrates that the product yield from the gas phase equilibrium-limited reaction for hydrogenation of mesitylene can be significantly increased using reactive SMB.

A. V. Kruglov, M. C. Bjorklund, R. W. Carr, Chem. Eng. Sci., Vol 51, 2945–2950 (1996), demonstrates that reactive SMB can be used to increase the product yield with the gas phase reaction for oxidative coupling of methane.

The feasibility of the condensation of phenol with acetone to form bisphenol-A and water and the simultaneous separation of the products has been considered through a numerical simulation (Kawase, M.; Inoue, Y.; Araki, K.; Hashimoto, K. Catalyst Today 1999, 48, 199–209).

Despite these advantages, the traditional SMB techniques have certain drawbacks. The traditional SMB configuration has always been defined as a plurality of beds connected in series and employing a unidirectional fluid flow. The SMB flow pattern also leads to many drawbacks such as high pressure drop, limited flow rate range, difficulty removing strongly adsorbed species, lack of tolerance for solids in the streams and incapability of optimizing conditions for both separation and reaction separately. This limited configuration inherently prevents the system from handling many reaction/separation applications, such as those that require high mass flow, toxin removal, and individual optimization of reaction and separation conditions. With these applications, the traditional SMB reactor system becomes very complicated, very expensive, and sometimes impractical. Furthermore, none of the present technologies allows for a continuous reaction and separation process using contacting beds arranged in parallel, rather than series, having reverse flow capabilities, or combination unit capabilities. Accordingly, it is an object in one embodiment of the invention to provide a process for performing combined reaction and separation that further provides parallel fluid flow, reverse flow, or combination unit design, or a combination of any of these thereby eliminating many of the prior art limitations. It is a further object in an embodiment of the invention to provide a process for performing combined reaction/separation step in a single processing unit to greatly decrease processing cost while increasing throughput.

SUMMARY OF INVENTION

Generally, the present invention provides a reactive chromatography process for performing the dual functions of chemical reaction and separation, either simultaneously or sequentially, to separate a single compound or multiple compound fluid mixture into components using a plurality of beds or columns packed with a solid or mixture of solids media and being independently connected in a either a series or parallel configuration. A compound is introduced into a column or group of columns that move or rotate to simulate a media flow. Compound moves in a fluid flow from one column to another column connected serially or parallel and in a direction opposite to the media flow thereby providing contact between the two phases in a countercurrent fashion. Compound is reacted and or separated in subsequent columns based upon its affinity towards the media to prepare a second component. Other feed material or eluent may be introduced depending upon the nature of the component and intended reaction/separation. The second component is then extracted from one or more of the columns and may include product, extract, raffinate, unconverted first component or combinations thereof.

The process utilizes columns for accepting flow from a connected column, an external stream feed, an external eluent stream or a combination thereof, and at least one outlet for connecting to another column, an external product stream or a combination thereof. Each of the columns is independently operable in an up-flow or down-flow mode and connects independently to another column, an external feed stream(s), an external client stream(s), an external product stream(s) or a combination thereof. The up-flow mode can be described by fluid flowing in the direction of the top of the column and the down-flow mode has a fluid flow from the top of the column in a general vertical direction downward. Independently connected can include a column or a group of columns each connected to another column, columns or group of columns or any other sources such as feed, external, event, or external products in any way the process requires without any preset flow pattern. The external product can be raffinate or extract or both. The flow configuration of each column can be modified to allow, for example, reverse fluid flow. In another example, the beds are arranged to create a combination unit design configuration. In still another example, the process provides for a parallel fluid flow configuration wherein at least one of the beds is connected in parallel. In another example, the process uses a combination of these configurations.

The beds preferably contain a solid or mixture of solids that act as a catalyst for the desired reaction and an adsorbent or separation media for removing the reaction product or other desired components. There are a wide variety of solid catalysts and adsorbents available. Such materials include, but are not be limited to, activated carbon, silica gels, aluminas, zeolites, zirconias, titanias, silicates, diatomaceous earths, and ion exchange resins. In one embodiment, a solid is preferred where it sufficiently performs both the catalytic and adsorbent functions. Where two or more solids are used, one performs the catalyic function while the other performs the separation function. These materials are chosen to provide enhanced reaction and separation over a single material. Also, it is possible that the solid acts only as a separation medium and the catalyst is not part of the solid phase but rather is dissolved in the liquid phase.

In an embodiment, the process uses one or more eluents to selectively desorb the reaction products, byproducts, or contaminants from the bed using an isocratic elution or a gradient elution process. The eluent comprises or contains a liquid capable of displacing such reaction product, byproduct, or contaminant from the adsorption bed. Examples of eluents include, for example, alcohols, ketones, esters, aliphatic hydrocarbons, aromatic hydrocarbons, ethers, carboxylic acids, halogenated hydrocarbons, amides, nitriles, water, or buffered solutions. Mixtures of eluents may also be used.

The feedstock supplied in an example of the invention is a single compound or multiple compounds as either a neat material or a solute in solution. It may include a wide variety of materials such as commercial chemicals, fine chemicals, drugs, pharmaceuticals, agrochemicals, foodstuffs, perfumes, flavors, fragrances, odorants, colorants, petrochemicals, etc.

This process is useful for conducting various types of reactions. In examples of the invention, the process is run with one or more of the reactions set forth below in Table 1.

TABLE 1

Esterification:

Methanol + Acetic Acid δ Methyl Acetate + Water
Ethanol + Acetic Acid δ Ethyl Acetate + Water
Butanol + Acetic Acid δ Butyl Acetate + Water
$\harpoon$-Phenethyl Alcohol + Acetic Acid δ $\harpoon$-Phenethyl Acetate + Water Ester Hydrolysis:

Methyl Acetate + Water δ Methanol + Acetic Acid
Ethyl Acetate + Water δ Ethanol + Acetic Acid
Butyl Acetate + Water δ Butanol + Acetic Acid
$\harpoon$-Phenethyl Acetate + Water δ $\harpoon$-Phenethyl Alcohol + Acetic Acid Etherification:

t-Butyl Alcohol + Methanol δ Methyl t-Butyl Ether (MTBE) + Water
Isoamylene + Methanol δ t-Amyl Methyl Ether (TAME)

Isomerization:

(ortho, para) Bisphenol-A δ (para, para) Bisphenol-A

Condensations:

Phenol + Acetone δ Bisphenol-A + Water
Methanol + Acetic Acid δ Methyl Acetate + Water
Ethanol + Acetic Acid δ Ethyl Acetate + Water
Butanol + Acetic Acid δ Butyl Acetate + Water

TABLE 1-continued

‡-Phenethyl Alcohol + Acetic Acid ẟ ‡-Phenethyl Acetate + Water
t-Butyl Alcohol + Methanol ẟ Methyl t-Butyl Ether (MTBE) + Water
Amide Synthesis:

Aniline + Acetic Anhydride ẟ Acetanilide + Acetic Acid
Dehydration:

t-Butyl Alcohol ẟ Isobutylene + Water
Oxidation:

Cumene + Oxygen ẟ Phenol + Acetone

In an example, the present invention is used in combination with a liquid-solid contacting device for directing fluid streams through a solid or mixture of solids media in a continuous or substantially continuous way. Some systems use multiple columns and a plurality of valves. Others use bed sections stacked in a vertical tower and fed by a rotary valve. A general review of the various devices can be found in U.S. Pat. No. 5,676,826, which is incorporated herein by reference. Any of the devices can be used with the present invention to achieve the desired continuous reaction and separation. Other embodiments of the invention perform the process in devices disclosed in U.S. Pat. Nos. 5,676,826; 4,808,317; 4,764,276; 4,522,726 and 6,431,202. U.S. Pat. No. 6,431,202 is incorporated herein by reference. In an example, the media "moves" by indexing of the columns in a manner that takes place so quickly as to be considered continuous.

In an embodiment, the process uses a liquid-solid contacting apparatus, such as described above, having a plurality packed columns each of which has a supply conduit and a discharge conduit adapted for connection to a disk having a plurality of ports associated with supply and discharge conduits. At least one of the columns or disks is mounted for rotation about an axis so that by rotation the conduits and ports in the disk are alignable for direct flow communication therebetween such that a plurality of supply and discharge conduits communicate with associated supply and discharge conduits of the columns and, by synchronizing rotation, at least the columns and the disk therein comprise flowing a process material through each of the columns to react and separate said flow material.

Particularly, when used with the present process, this device allows for a wide variety of processing possibilities that have not been taught in the prior art of combined reaction/separation technologies. Unlike the traditional SMB, series connection that forces reactant solvents through the system in a serial mode and unidirectional fluid flow, the present invention incorporates parallel liquid flow, reverse liquid flow, and/or combination unit configuration, as single or multiple zones and in any combination within a single unit thereby eliminating many of the prior art limitations. These unique capabilities are especially advantageous in that the present invention is not limited to a series bed arrangement or unidirectional fluid flow, as is the prior art. It allows use of a process stream which contains certain amount of solids, and makes removal of highly adsorbed species easier and more economical. In addition, an embodiment of the process reduces the elution consumption, increases the feed rate and reduces pressure drop. This significantly simplifies the reaction separation processes providing more efficient operation. This flexibility advantageously increases productivity, reduces capital and operational costs and improves product quality over traditional processes. In particular, in an example, the present invention offers significant capital cost savings for equilibrium limited, reactant/product inhibited processes. Other features, aspects and advantages of embodiments of the present invention will become better understood or apparent from a perusal of the following detailed description and examples of the invention and appended claims.

DESCRIPTION OF EXAMPLES OF THE INVENTION

The present invention provides a process for chemical reaction and separation using multiple beds or columns comprised of a solid or mixture of solids connected in series, parallel, or combination of such configurations. The reaction/separation can occur concurrently or sequentially. The beds are configured to have a reverse flow, or a combination unit or a parallel flow configuration or any combination thereof. In embodiment, the invention is used in combination with a continuous liquid-solid contacting device. The present invention can be used with a variety of different types of reactions. Examples of some of the types of reactions that can be used with this process are shown above in Table 1. The examples below further show the various configurations of the process. One skilled in the art would appreciate that flows demonstrated by each configuration may be used alone or in combination with any of the others to carry out the reactions set forth in Table 1 and others.

EXAMPLE 1

Reverse Flow Configuration

In an embodiment of the present continuous reaction/separation process, a unit having multiple columns packed with a catalyst and adsorbent is designed to operate with a liquid flow of reactants and a solid or solid-containing resin catalyst fixed in the columns which move to facilitate the process and a flow reverse which changes the direction of the liquid flow relative to the other liquid flow in the system. The columns provide zones for reacting and or separating, eluting, enriching and, in this example, utilize a continuous solid contacting device enabling columns to index flow of process material enabling these reactions/separations.

Figure 2:
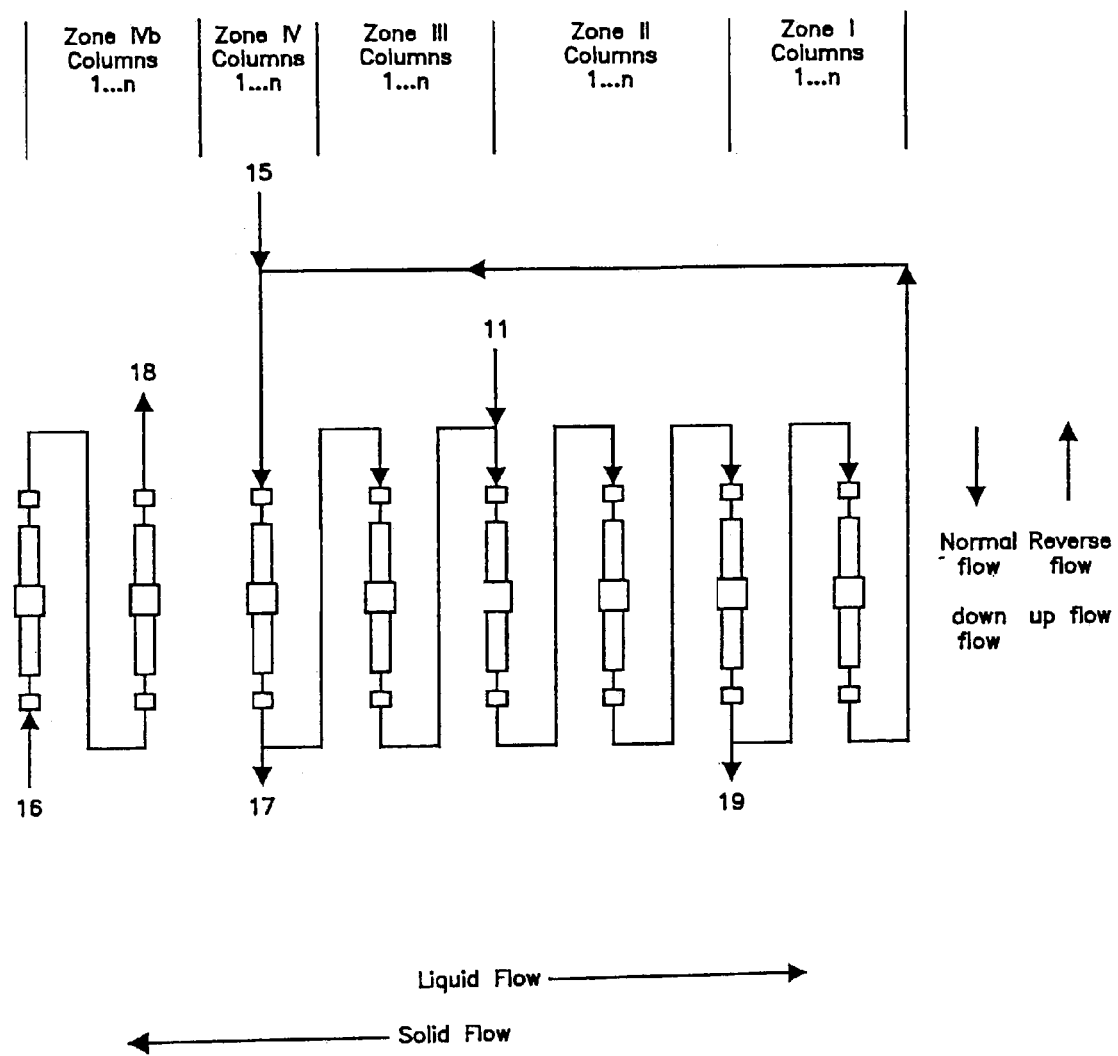
FIG. 2 shows a schematic representation of an embodiment of the present invention using a reverse flow configuration.

FIG. 2 illustrates one possible configuration for conducting the process with a reverse flow. This occurs in Zone IVb where columns operate in an up-flow, mode whereas the remainder of the columns in the unit operate in the downflow mode. This is just one example of the use of reverse flow.

A process designed with a reverse flow configuration provides a variety of uses. For instance, it can be used to remove very strongly adsorbed components. FIG. 2 illustrates a reaction with a reverse flow to produce one weakly adsorbed component and two strongly adsorbed components (one of which is more strongly adsorbed) which are separated and removed with eluent. Using this process the weakly adsorbed component moves with the liquid in the direction of the outlet 19 where it is removed as the raffinate product. The two strongly adsorbed components move with the solid flow in the direction of the extract outlets 17,18. The less strongly adsorbed component of the two moves with the solid in the direction of the outlet 17 where it is eluted from the system by eluent I fed into inlet 15 and is extracted as extract I product at outlet 17. The more strongly adsorbed component of the two continues to move past the extract I outlet 17 in the direction of the outlet 18. This component is eluted by eluent II fed into intake 16 and is extracted as extract II at outlet 18. These components may include a product, byproduct, inhibitor, contaminant, etc.

An esterification reaction illustrates one of the advantages of the reverse flow configuration:

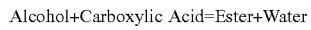
Alcohol+Carboxylic Acid=Ester+Water

In this example, alcohol and carboxylic acid act as feed which is introduced into the top of the column 11. The water together with another strongly adsorbed species, moves with the solid in the direction of outlet 17. Eluent I is introduced at column 15 to extract water at outlet 17 as extract I product. A more weakly adsorbed product, the ester, is also generated by the chemical reaction. It moves with the liquid flow in the direction of raffinate outlet 19 where it is collected from the system as raffinate product. In this case the alcohol could also be used as the eluent I introduced into the process at intake 15, which will remove the water from the solid phase as extract at outlet 17 and also act as a liquid carrier for the rest of the system.

The more strongly adsorbed component will accumulate at the top of the column(s). Then, eluent I or a different eluent, eluent II, is directed into the process at intake 16, in a reverse flow to elute this more strongly adsorbed component out of the top of a column at outlet 18 as extract II. Elution of extract II at outlet 18 from the top of the column eliminates the need for the eluent II to carry the more strongly adsorbed component all the way through the series of columns to effectuate its removal, as is required in the traditional SMB process. Instead, the reverse flow provided in Zone IVb decreases the length of time for the elution or amount of eluent necessary to complete the process thereby resulting in decreased cost and improved productivity and efficiency of the elution step. Further, in an embodiment of the process, this reverse flow configuration can also accommodate two different eluents for desorption of the two different strongly adsorbed components.

The use of the reverse flow configuration is not limited to the previous specific example. Those skilled in the art would realize that, with the present invention, the unique reverse flow configuration can advantageously be incorporated anywhere within the process: elution zone, reaction zone, separation zone, and the like. Because traditional SMB is carried out with unidirectional flow, the present technique is outside of the realm of traditional SMB.

Embodiments of the process incorporating reverse flow configuration provide the user with certain advantages. The reverse flow process, for example, is useful to remove solids that would accumulate on the top of the column(s), therefore allowing the use of a process stream which contains a certain amount of solids or a process stream which has the potential to form solids in the course of the reaction/separation process. In this way solids can be removed continuously from the top of the column, thereby overcoming a disadvantage of the traditional SMB system which is limited to a unidirectional liquid flow. The SMB process does not allow for continuous removal of solids. The solids would either be trapped in the unit or plug the liquid flow all together.

A reverse flow process can be effectively utilized in a different zone or in multiple zones depending upon the desired reaction and adsorption strengths of particular components. It is not restricted to the specific reverse flow configuration shown in FIG. 2. This process flexibility and versatility will be realized by those skilled in the art to adapt many different possible variations.

EXAMPLE 2

Parallel Flow Configuration

Figure 3:
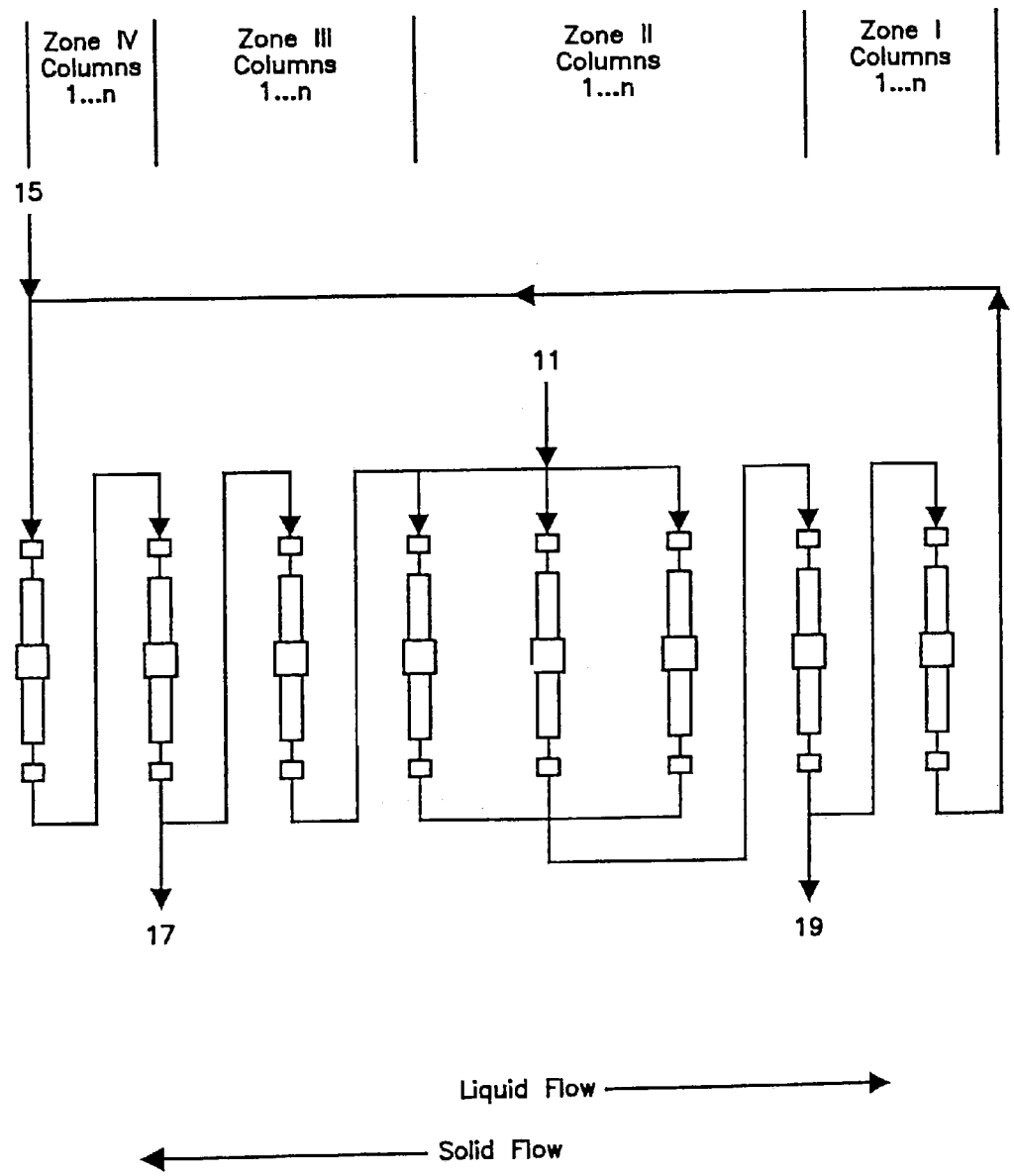
FIG. 3 shows a schematic representation of an embodiment of the present invention using a parallel flow configuration.

In another embodiment of the present process, reaction and or separation is carried out through a series of columns and multiple columns connected together to provide for a parallel flow in part of the process. As shown for example in FIG. 3, part of Zone II is arranged in parallel. Feed is introduced into several columns, 11i a, 11b, and 11c, connected in parallel to other columns in series. An eluent is introduced into the process at intake 15 to extract products or byproducts at outlet 17. Meanwhile, weakly adsorbed components, raffinate, move with the liquid and are extracted at outlet 19. The components of the process system can, either alone or alternatively in combination, employ parallel flow, including the feed, eluent, raffinate, or extract streams.

In an example parallel flow process offers the ability to obtain high flow rates while maintaining an acceptable pressure drop and reaction performance for the process. These capabilities prove especially useful for reactions that require long hold-up time and high mass flow. Such reactions can encounter high pressure drops when performed using the prior art configuration where the columns are connected in a series configuration. The pressure drop requirement for a given process is a very important design parameter. As the pressure drop requirement increases, the cost of the equipment increases and, at some point, the process becomes impractical or even impossible. In an embodiment of the invention parallel flow process is advantageously employed to reduce the cost of the equipment and increase its productivity. In processes where a reduction in pressure drop is not required, the parallel flow configuration allows for higher productivity at a given pressure drop.

EXAMPLE 3

2-in-1 Configuration (Type A)

In another embodiment, the present reaction and or separation process is designed to conduct a reaction/separation or an additional reaction/separation in a zone separate and independent from others. This independent sub-process occurs in one or multiple columns of Zone V which are connected together separately inside of a separation train, as shown for example in FIG. 4. This combination unit configuration is also referred to herein as a "2-in-1 flow configuration." The 2-in-1 flow configuration optimizes the reaction and separation operations by allowing each reaction/separation to be carried out under different conditions. In addition to reaction/separation, another reaction may be conducted, i.e., reaction/separation/reaction or 3-in-1. This process configuration is not limited to 2-in-1 or 3-in-1, but may be used to perform multiple reactions and separations in N-in-1 configuration, where N is an integer greater than 1.

For example, the feed is directed into column II which is not connected directly in series with the column that precedes it, but rather is connected independently into the liquid flow of the system. Thus, the user can vary the hold-up time, the composition, and the temperature for the reaction in the column 11 without limiting the conditions that can be applied to the rest of the process.

In an example, the 2-in-1 process flow combines a fixed bed type reactor and SMB type separation reactor into a single unit to provide a separate reaction zone that is generally in the middle of the separation/reaction process. In this arrangement, by reference to FIG. 4, feed is introduced into the top of column II to act as a fixed bed reactor that feeds a reaction product to an SMB unit for separation and additional reaction as needed. The separate reaction occurs in Zone V, as shown for example in FIG. 4. The advantage of feeding the fixed bed reacted product into a separate SMB unit has been partially realized in prior art, such as in U.S. Pat. No. 5,618,972, by conducting the operation in two units. This 2-in-1 flow combination improves the effectiveness of the fixed bed reactor while also improving the cost efficiency of the SMB unit. The present invention further improves this process by combining two units into a single unit. It eliminates the costs associated with maintaining two freestanding units that are then physically connected together.

An example of the 2-in-1 processes is illustrated by an esterification reaction:

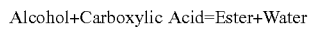

Alcohol+Carboxylic Acid=Ester+Water

Alcohol and carboxylic acid are fed into column 11 and reacted in Zone V to produce water and ester. Water is the more strongly adsorbed product and therefore moves with the solid flow in the direction of extract outlet 17 where it is eluted as extract I product. The ester, raffinate product, is the weakly adsorbed product and moves with the liquid in the direction of the raffinate 19 outlet. In this case, the alcohol could also be used as the eluent I introduced at intake 15. Because this 2-in-1 configuration provides for a feed column that is not directly connected in series, it allows the user to optimize the process parameters for the reaction zone independently from the process parameters that are required for the separation by being able to adjust the temperature, hold up time, and feed composition. This type of process flexibility where one can carry out reaction and separation in one unit while still being able to separately optimize process conditions for each, is not realized with traditional SMB processes that, by definition, entails columns connected in series.

Those skilled in the art will realize that this technique can be advantageously applied to wide variety of reactions, such as esterification, ester hydrolysis, etherification, isomerization, condensations, amide synthesis, peptide synthesis, dehydrations, oxidations just to name a few. It will also be realized that the use of the present invention is not restricted to the specific configuration shown in FIG. 3. Those skilled in the art will realize that many different variations are possible because of the flexibility and versatility of the present invention.

EXAMPLE 4

2-in-1 Configuration (Type B)

In another embodiment of the present invention, one or multiple columns are connected together in a zone that is still within the same unit but outside the separation process zone. The 2-in-1 flow configuration (type A) shown in Example 3 incorporates a reaction zone into the middle of a traditional SMB process. The composition of the material in the reaction zone is influenced by the composition of the adjacent column which will move into the reaction zone position. The columns index in the direction of the solid flow. With the 2-in-1 flow configuration (type B), by reference to FIG. 5, the reaction zone, Zone V, receives the next column from elution in Zone I. For example, this process provides for a pre-reaction. Precursor materials can be introduced into column 12 where a pre-reaction occurs in Zone V outside of the reaction/separation process. The pre-reaction generates feed which is then introduced into the reaction/separation process at inlet 11. This pre-reaction process can be advantageously conducted under different conditions and performed more efficiently because it lacks influence from the rest of the process. This process feature gives the reaction zone a clean column rather than a column that already contains a certain composition of material. This allows for additional process optimization that goes beyond the 2-in-1 (type A) configuration. This type of process is also outside the traditional SMB process which relies on columns that are endlessly connected in series. The prior art of reactive SMB does not teach use of this type of configuration as it would not necessarily be advantageous under its limited operating conditions.

Figure 5:
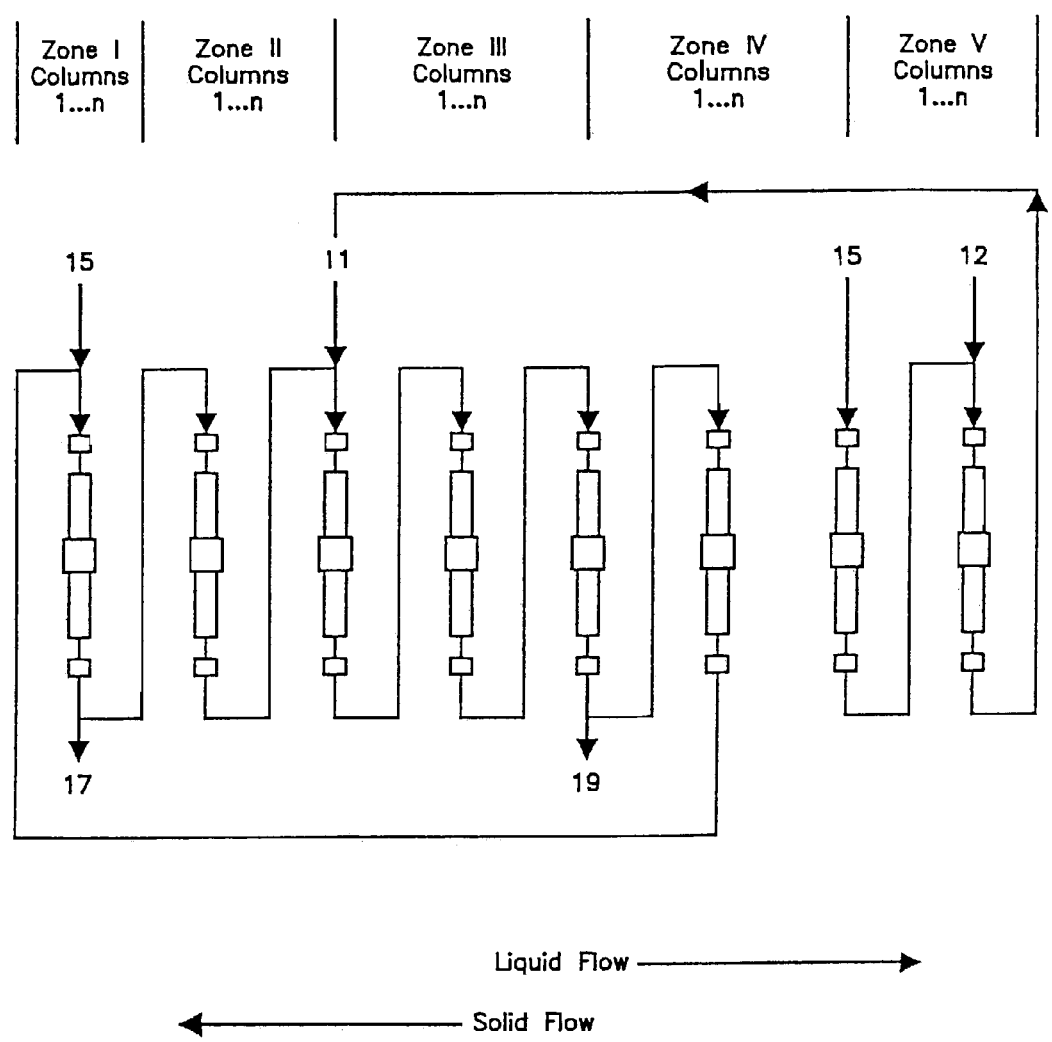
FIG. 5 shows a schematic representation of an embodiment of the present invention using another combination unit design.

The use of the present process in this flow configuration is not restricted to the specific configuration shown in FIG. 5. Those skilled in the art will realize that many different variations of 2-in-1 configurations are possible because of the flexibility and versatility of the present invention.

EXAMPLE 5

The following example illustrates one of the benefits of conducting the present process in a non-SMB flow configuration, such as with a fluid-solid contacting system. In particular, the High Performance Carousel-SMB (HPC-SMB) provided by Calgon Carbon Corporation was used, but should not be seen as a limitation. Using the HPC-SMB containing a strong acid ion exchange resin, phenol was reacted with acetone to produce bisphenol-A (BPA). Such resins are available from Rohm & Haas, Dow, Bayer, and Mitsubishi, among others. Amberlyst 131 resin from Rohm & Haas is used in this experiment. The results are shown in Table 2.

Figure 6:
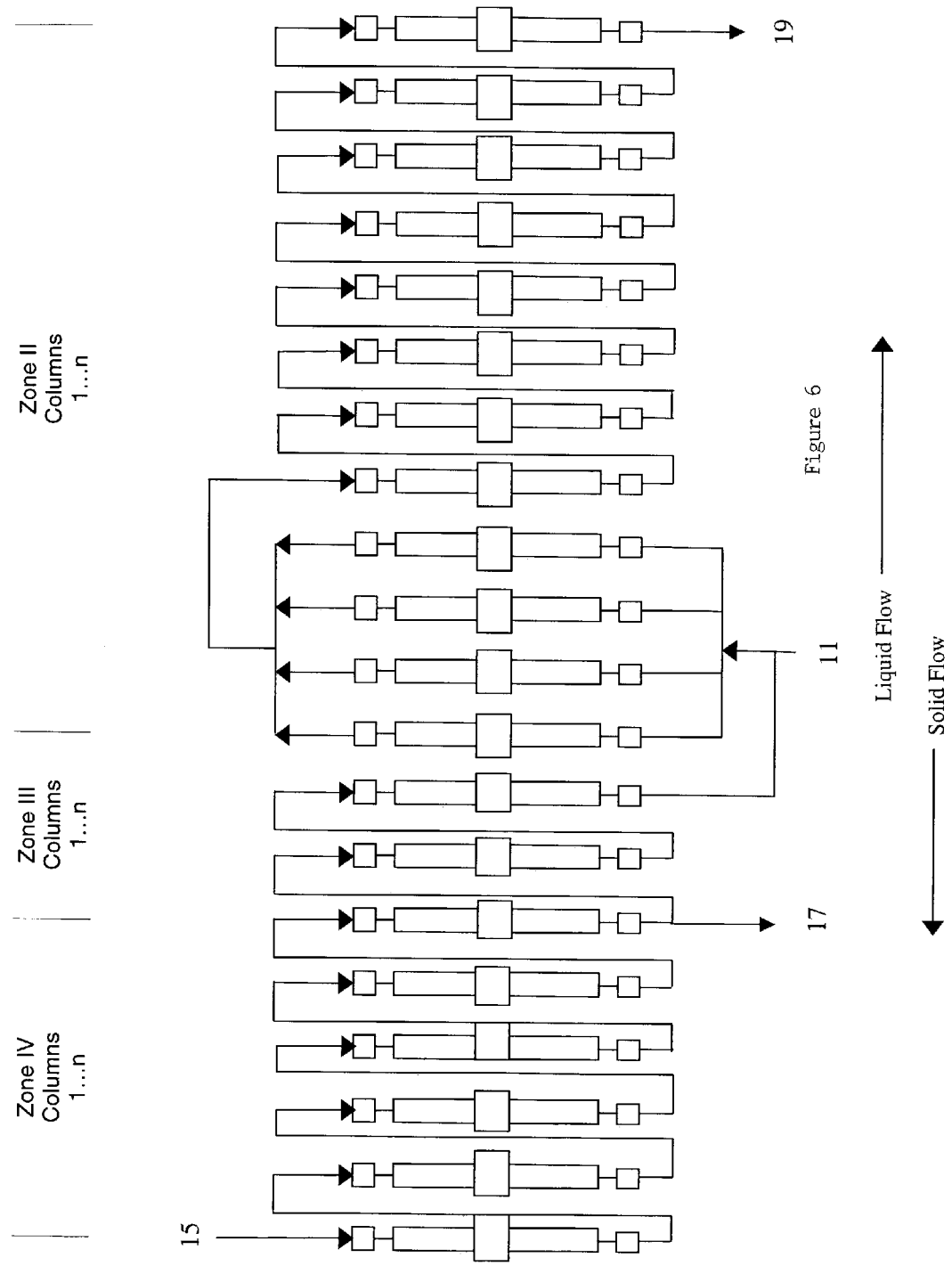
FIG. 6 shows a schematic representation of an embodiment of the present invention that combines a series flow configuration with a parallel flow configuration that uses a reverse flow mode.

In this embodiment, the unit contains a set of 20 columns that are each 11 mm in diameter and 300 mm in length. As illustrated in FIG. 6, the elution zone (Zone IV) contains 6 columns, the enrichment zone (Zone III) contains 2 columns, and the reaction zone (Zone II) contains 12 columns. The unit is contained in an enclosure that was maintained at a constant temperature. The acetone is fed to the reaction zone at feed inlet 11 where a condensation reaction with phenol occurs to form BPA. The strongly adsorbed water is continuously carried out of the reaction zone and into a water election zone by a counter current movement of the resin catalyst against the flow of reactants. In the water elution zone, adsorbed water is removed from the resin with the phenol at outlet 17. Enough makeup phenol is added at intake 15 to the elution zone to both dehydrate the resin and to provide enough excess phenol for the reaction zone. The water tends to hydrate the catalytic sites which decreases the activity of the resin catalyst.

Downstream of the reaction zone, the crude BPA product as well as excess phenol are extracted from the process at outlet 19. A portion of the extracted product can optionally be passed to a reload zone to flush phenol from the resin bed and reduce dilution of the product. This example illustrates the improvement in product yield and purity.

Figure 1:
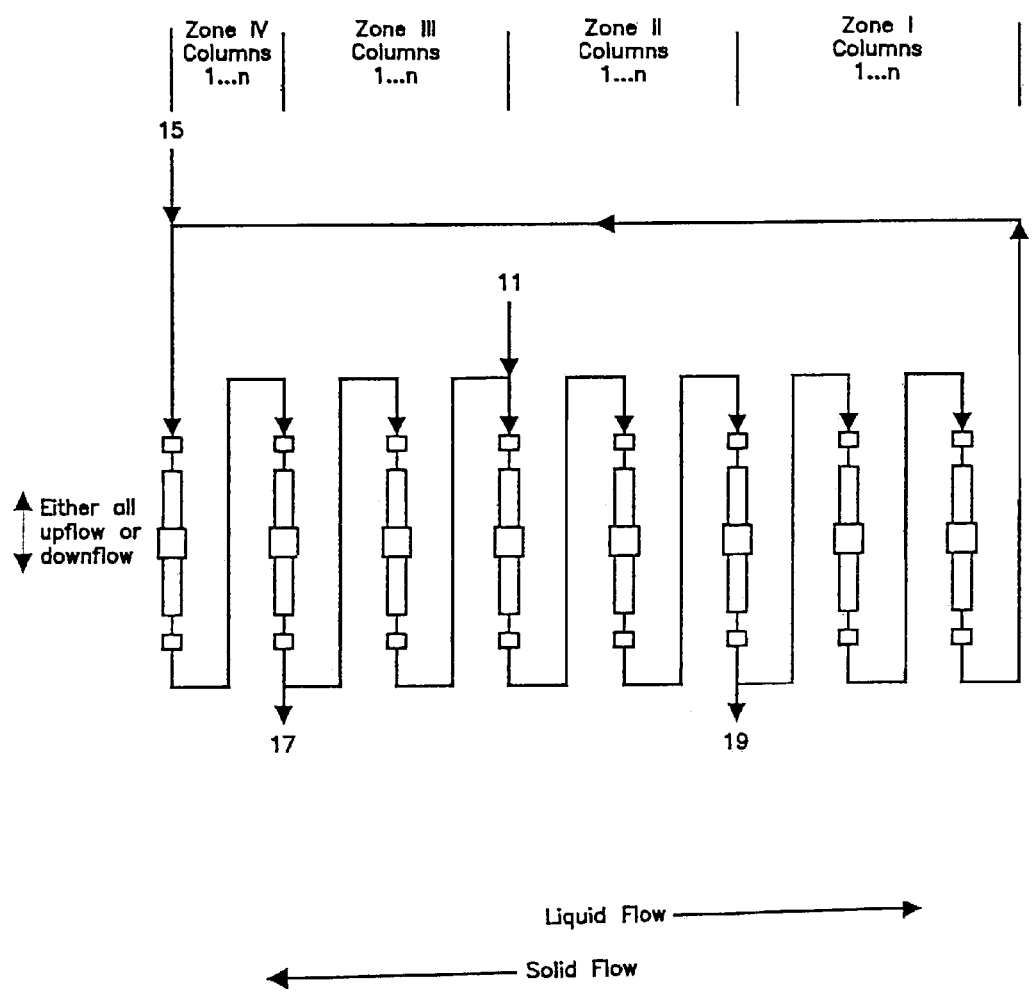
FIG. 1 shows a schematic representation of a prior art configuration of a general SMB process.
Figure 4:
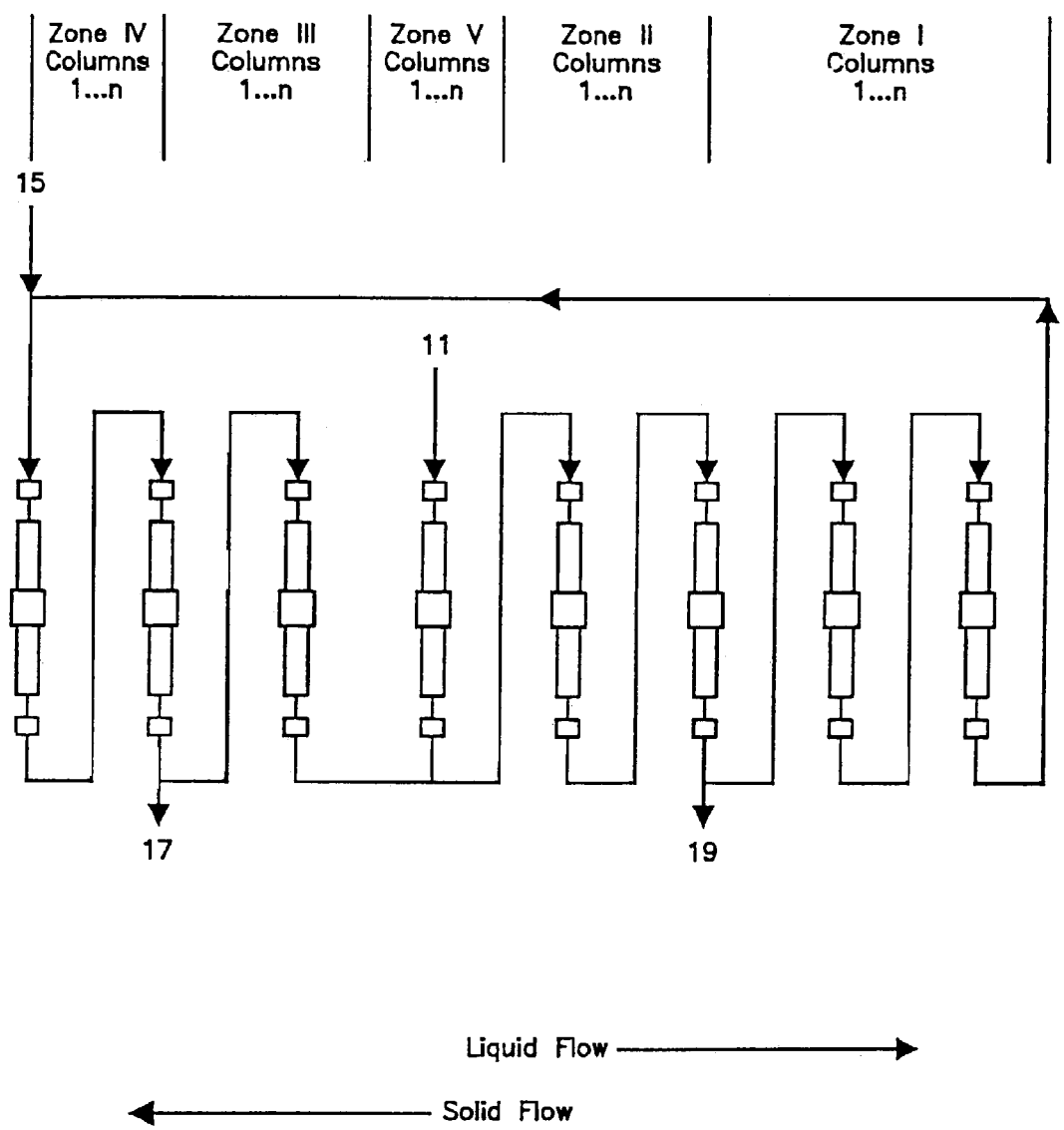
FIG. 4 shows a schematic representation of an embodiment of the present invention using a combination unit design.

The use of the traditional SMB flow configuration requires that all of the columns be connected endlessly in a series flow configuration as shown in FIG. 1. The present process combines series, parallel and/or reverse flow configurations together in one unit. The parallel flow configuration is illustrated in FIG. 4 and the reverse flow configuration is illustrated in FIG. 2. For this example, by reference to FIG. 6, the first 4 columns in the reaction zone are connected in a parallel flow configuration and the remaining 8 columns are arranged with the series flow configuration. The parallel flow columns are also run with the reverse flow configuration (up-flow). This allows for an improved distribution of reactants and products that increases the yield of the BPA product while reducing the level of impurities. The product compositions were determined using high performance liquid chromatography (HPLC). Table 2 shows a comparison of the results obtained from this example of combining series flow and (partial) parallel flow/reverse flow configurations. The same feed rates for the phenol and acetone are used in both experiments.

TABLE 2

| | Phenol free composition of products | | |
|---|---|---|---|
| | BPA wt % | Impurities wt % | % Acetone Conversion |
| Series flow | 92.0 | 8.0 | 80 |
| Parallel flow | 93.5 | 6.5 | 80 |

The higher BPA yield and lower level of impurities are both desirable results for this reaction.

The previous examples illustrate the versatility of the present invention. Although the illustrations depict a particular example of each configuration or a combination of configurations, those skilled in the art will realize that a number of variations are possible within the scope of this invention. Any given configuration may contain more or less zones than shown in FIGS. 2–5. Each zone may contain anywhere from one to zero to multiple columns. Typically, systems utilize four zones, and sometimes only three. In this example, the missing zone contains zero columns. In the present invention, special function zones (reverse flow, parallel flow, etc.) may be used anywhere in the system and are not limited to the location shown in the illustrations. More than one configuration may be used in a unit and multiple functions can be combined in one unit.

Those skilled in the art, will realize that this level of process flexibility becomes very complicated and very expensive with the traditional SMB technologies. The advantages listed above will result in reduced capital costs, higher productivity, higher yields, and improved selectivity.

Those skilled in the art will also realize that the present invention can be used with many different reaction/separation applications. For instance, the present invention can be used for, but not limited to, esterification, ester hydrolysis, etherification, isomerizations, condensations, amide synthesis, peptide synthesis, dehydrations, and oxidations just to name a few.

While the foregoing has been set forth in considerable detail, the examples and methods are presented for elucidation and not limitation. It will be appreciated from the specification that various modifications of the invention and combinations of elements, variations, equivalents, or improvements therein may be made by those skilled in the art, and are still within the scope of the invention as defined in the appended claims.

What is claimed is:

1. A process for the production of reaction products and separation products from a chemical reaction and separation using a liquid-solid contacting apparatus which comprises:
   (a) inputting a non-ionic process material into at least one column of a plurality of columns packed with media, each said column having at least one inlet for accepting a flow of said process material from another column or group of columns, an external feed stream, an external eluent stream or a combination thereof, and at least one outlet for connecting to another column, a group of columns, an external product stream or a combination thereof; each said column being independently operable in an up-flow or down-flow mode and connected independently to one of the group comprising another column, an external feed stream, an external eluent stream, an external product stream and combinations thereof, wherein at least two of said column inlets are available to selectively create a parallel flow respectively therethrough and wherein some but not all said columns are connected in series having a unidirectional flow respectively therethrough;
   (b) reacting and separating said non-ionic process material in one or more said columns; and
   (c) extracting non-ionic material therefrom.

2. A process for the production of non-ionic reaction products and non-ionic separation products by a substantially continuous chemical reaction and separation using a plurality of columns having upper and lower ports to selectively serve as inlets or outlets that selectively connect one or more of said other columns for upflow or downflow therethrough and wherein some but not all said columns are serially connected for unidirectional flow, said process comprising:
   (a) directing at least one non-ionic process material into an inlet of at least a first selected column;
   (b) initiating separation of said non-ionic process material in at least said first selected column;
   (c) reacting said non-ionic separation product wherein said reaction product accumulates in one or more columns; and
   (d) extracting said non-ionic reaction product therefrom.

3. A process for the production of reaction products and separation products by a substantially continuous chemical reaction and separation using a plurality of columns having upper and lower ports to selectively serve as inlets or outlets that selectively connect one or more of said other columns for upflow or downflow therethrough and wherein some but not all said columns are serially connected for unidirectional flow, said process comprising:
   (a) directing at least one non-ionic process material into an inlet of at least a first selected column to prepare a non-ionic reaction product;
   (b) initiating a reaction of said non-ionic process material in at least said first selected column;

(c) separating said non-ionic reaction product wherein said non-ionic reaction product accumulates in one or more columns; and (d) extracting said reaction product therefrom.

4. A process for the reaction and separation as set forth in claim 2 or 3 wherein said columns are configured to provide at least one reverse flow.

5. A process for the reaction and separation as set forth in claim 2 or 3 wherein at least two said columns are connected to said flow therein in parallel to provide a parallel flow configuration.

6. A process for the reaction and separation as set forth in claim 2 or 3 having a first separation/reaction process zone and wherein a single column or multiple columns are connected together to provide at least a second separate reaction zone within said first separation/reaction process zone.

7. A process for the reaction and separation as set forth in claim 2 or 3 having a separation/reaction process zone, wherein single or multiple columns are connected together in a zone within said unit but outside of said separation/reaction process zone.

8. A process for the reaction and separation as set forth in claim 2 or 3 having a separation/reaction process zone, wherein one or more said columns are connected to provide a flow therethrough selected from the group consisting of: reverse flow, parallel flow, a separated reaction zone inside of a separation/reaction process zone, separated reaction zone in a zone within said unit but outside of said separation/reaction process zone, and a combination of any one or more of these configurations.

9. A process as set forth in claim 4 wherein said process flow contains solids or forms solids in the course of the process.

10. A process as set forth in claim 9 wherein said solids are removed from the top of at least one column, said removal being either continuously or intermittently.

11. A process as set forth in a claim 2 or 3 wherein said columns are moveably connected serially or parallel to a proceeding column or an external stream to simulate a media flow by rotating to from one to the next.

12. A process as set forth in claim 1, 2 or 3 for the production of bisphenol-A.

13. A process as set forth in claim 12, wherein at least two said columns are connected in parallel to columns connected in series configuration, said parallel columns having a fluid flow direction opposite to said media flow or toward the top of said parallel column.

14. A process as set forth in claim 12, having a process material comprising acetone and an eluent comprising phenol.

15. A process as set forth in claim 2 or 3 wherein said steps (a), (b) and (c) are conducted simultaneously, or are conducted in any order.

16. A process as set forth in claim 2 or 3 further including the additional step of inputting a second non-ionic material into at least a second of said columns.

17. A process as set forth in a claim 1, 2 or 3 wherein at least one said columns contains a catalyst, adsorbent, separation media or combination thereof selected from the group consisting essentially of activated carbon, silica gels, aluminas, zeolites, zirconias, titanias, silicates, diatomaceous earths, and ion exchange resins.

18. A process as set forth in a claim 1, 2 or 3 having an eluent selected from the group consisting of alcohols, ketones, esters, aliphatic hydrocarbons, aromatic hydrocarbons, amides, nitriles, water or buffered solutions, and mixtures thereof.

19. A process as set forth in a claim 1, 2 or 3 further including the step of flowing an eluent counter current to said first component or said process material.

* * * * *